United States Patent [19]

Ness

[11] Patent Number: 4,525,407

[45] Date of Patent: Jun. 25, 1985

[54] ELASTIC COMPOSITES

[75] Inventor: Irving S. Ness, Palmetto Dunes, S.C.

[73] Assignee: Chicopee, New Brunswick, N.J.

[21] Appl. No.: 502,366

[22] Filed: Jun. 8, 1983

Related U.S. Application Data

[63] Continuation-in-part of Ser. No. 412,446, Aug. 27, 1982, abandoned.

[51] Int. Cl.³ .......................... B32B 3/24; B32B 3/28
[52] U.S. Cl. .................................... 428/138; 156/229;
  156/290; 428/152; 428/172; 428/198; 428/212
[58] Field of Search .............. 428/198, 179, 172, 152,
  428/212, 138; 156/229, 84, 160, 161, 290

[56] References Cited

U.S. PATENT DOCUMENTS 3,819,401 6/1974 Massengale et al. ............... 156/229
4,418,123 11/1983 Bunnelle et al. .................... 156/229

FOREIGN PATENT DOCUMENTS 54-125272 9/1979 Japan ................................. 156/229

*Primary Examiner*—Paul J. Thibodeau
*Attorney, Agent, or Firm*—Nancy A. Bird

[57] ABSTRACT

An extensible elastic composite with elastic recovery and process for making the same comprising intermittently securing an elastic member to a substrate which prior to initial stretching is easily less extensible than said elastic member.

16 Claims, 14 Drawing Figures

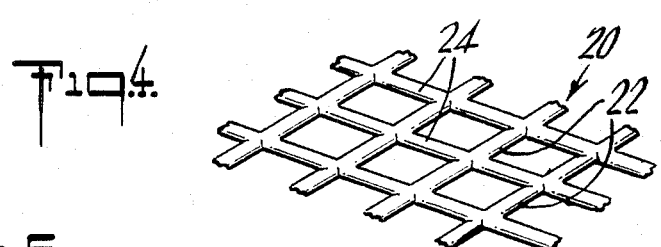
Fig.4.
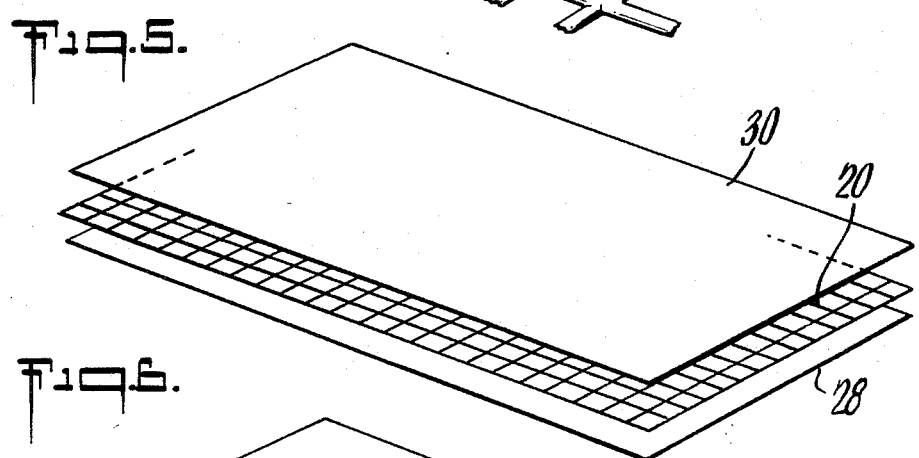
Fig.5.
Fig.6.
Fig.7.
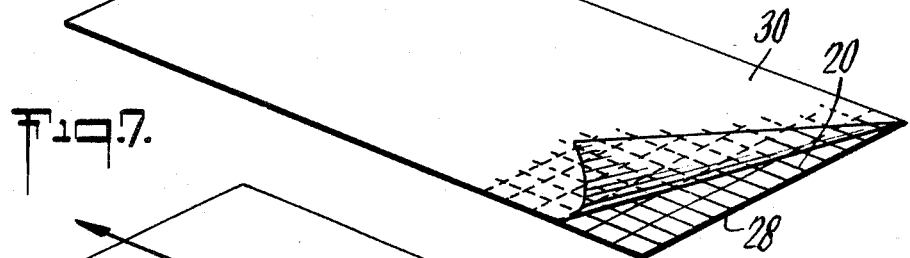
Fig.8.
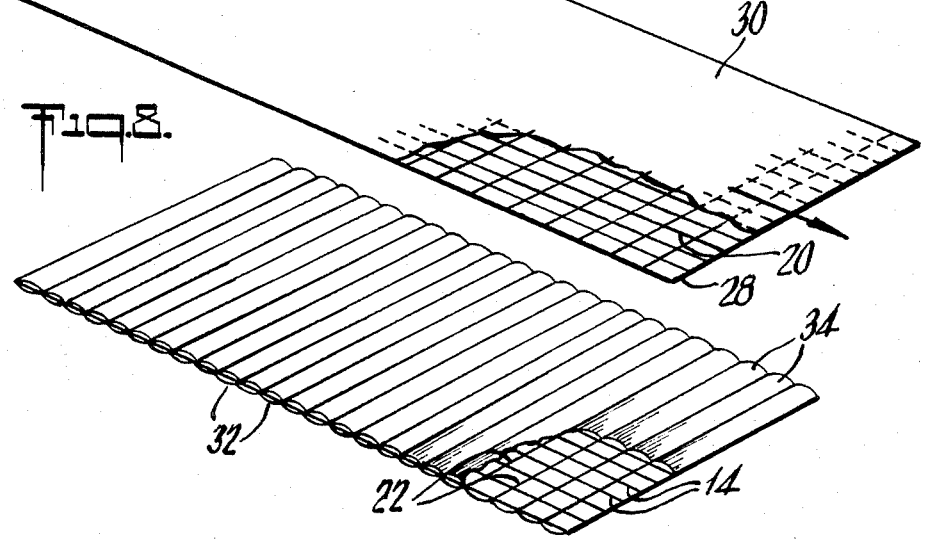

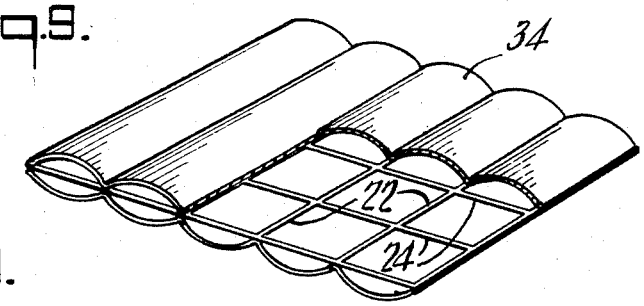
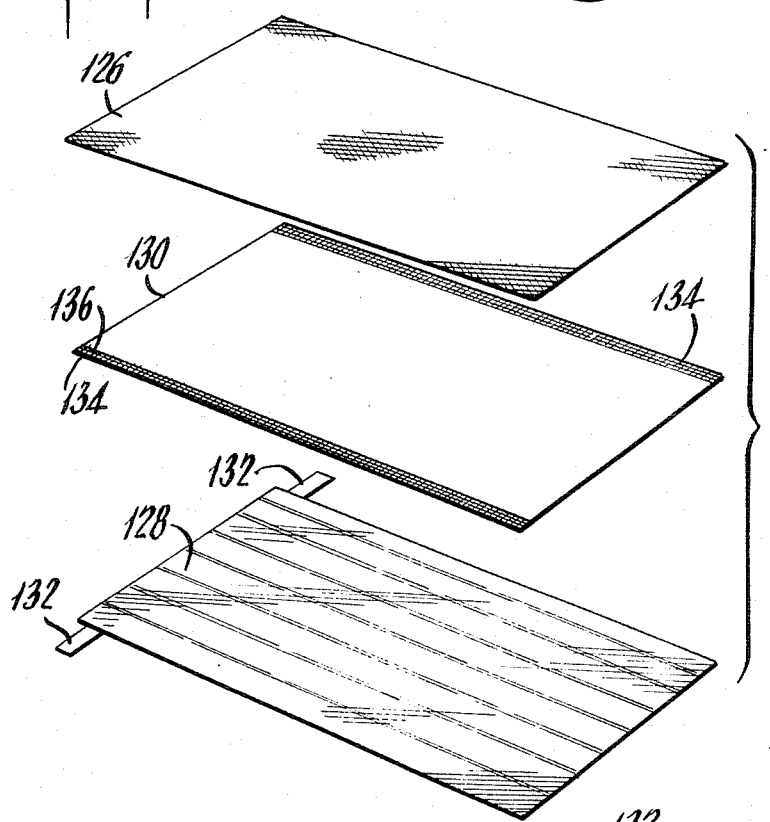
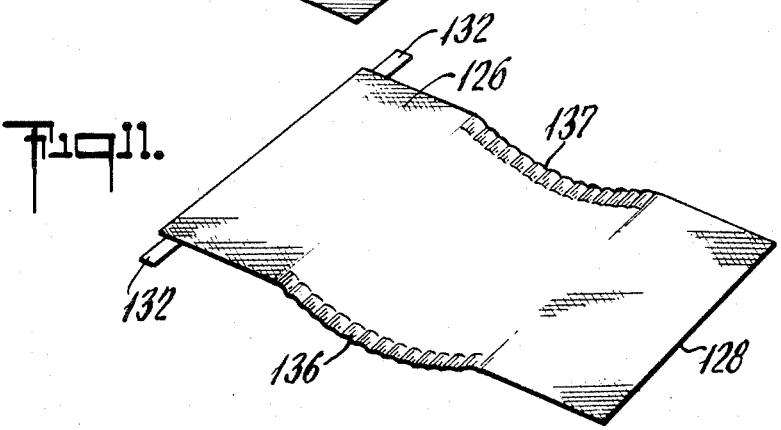

ELASTIC COMPOSITES

BACKGROUND OF THE INVENTION

This is a continuation-in-part application of U.S. Ser. No. 412,446, filed Aug. 27, 1982 abandoned.

Various articles, including disposable diapers, bandages, disposable examination and surgical gowns, clean room coveralls, etc., utilize elastic material to improve the conformability and fit. The improved conformability and fit enhance both the appearance and the functionality of the article. The present invention provides a new elastic composite and a new and easier method of incorporating elastic into these articles.

A preferred elastic material for use in the present invention is a reticulated elastic. Various reticulated or filamentary materials are disclosed in U.S. Pat. Nos. 3,255,065; 3,791,911; and 3,474,952. However, the reticulated or filamentary materials disclosed in these patents are not elastic and are used merely to reinforce film.

One method of incorporating elastic into disposable articles may be found in U.S. Ser. No. 60,704. In this application a stretched reticulated elastic is secured in a disposable diaper or undergarment imparting a predetermined elasticity to leg opening and/or waist portion of the diaper. In one embodiment of the elastic composite of the present invention, the elastic is secured within the composite in an unstretched condition. Unstretched elastic is easier and less expensive to handle during the manufacturing of the garment or composite. In addition, the position and degree of extensibility of the elastic composite of the present invention may be determined by the user. In a preferred method of the present invention the elastic member in a partial stretched condition is incorporated into the composite, and the composite is selectively stretched. Another method of incorporating elastic into an article involves securing an immobilized stretched elastic to a substrate as disclosed in U.S. Pat. No. 3,694,815. Thereafter, the means for immobilizing the elastic is removed and the elastic relaxes gathering the substrate. Still another method of incorporating elastic into articles is disclosed in U.S. Pat. No. 3,639,917 wherein a heat recoverable elastic material is secured to a substrate while in an unstretched condition and then heated. Both of these latter two methods involve the gathering or foreshortening of the substrate material to which the elastic is attached, as opposed to the present invention in which an unstretched elastic member is bonded to a substrate where the original length of the composite is never decreased.

BRIEF SUMMARY OF THE INVENTION

The elastic composite of the present invention comprises an elastic member intermittently bonded to a substrate which before stretching is less easily extensible than said elastic member, and which has a less elastic recovery than said elastic member. The elastic member may comprise a non-apertured elastic band or reticulated elastic. The composite formed and, particularly, the substrate may be initially stretched in selected regions and to a selected degree. After the initial stretching, the substrate and the composite may be retracted by the elastic member, but may be easily extended within the limits of the initial stretching of the substrate. In this embodiment of the invention the unstretched elastic is intermittently bonded to a stretched, puckered substrate. In a preferred embodiment, the substrate comprises a plastic film and in a still preferred embodiment, the plastic film has a low melting point component such as ethylene-vinyl acetate adjacent the elastic member. The composite may comprise a second substrate "sandwiching" the elastic. The composite may be used in the waist and/or the leg opening regions of a garment or disposable diaper; or in the wrist, armhole, or waist of a conformable garment, such as an examination or surgical gown; or in a bandage.

One embodiment of the process of the present invention comprises intermittently bonding an unstretched elastic member to an unstretched non-gathered substrate having less extensibility than said elastic member and with less elastic recovery than said elastic member. This process may further comprise stretching selected areas of the composite to a selected degree to give the composite an adjustable elasticity. In another embodiment of the process of the present invention, a partially stretched elastic member is intermittently bonded to a substrate which, prior to stretching, is less easily extensible than the elastic member to form an elastic composite, and thereafter stretching selected areas of the composite to a selected degree. The composite may be incorporated into garments or bandages during manufacture and may be selectably stretched prior to wearing or while worn. Alternatively, the composite may be selectively stretched before incorporation into a garment or bandage.

BRIEF DESCRIPTION OF THE DRAWINGS

FIG. 4 is a perspective view of a preferred elastic member for use in the present invention;

FIG. 5 is an exploded perspective view of an elastic composite according to the present invention;

FIG. 6 is a perspective view partially peeled away of the assembled elastic composite of FIG. 5;

FIG. 7 is a perspective view partially cut away of the elastic composite of FIG. 6, when stretched under tension;

FIG. 8 is a perspective view partially cut away of the elastic composite of FIG. 7, when the tension is released;

FIG. 9 is an enlarged view of a portion of FIG. 8;

FIG. 10 is an exploded perspective view of the elements of a disposable diaper incorporating the elastic composite of FIG. 1 along the longitudinal side edges;

FIG. 11 is a perspective view of the disposable diaper assembled as in FIG. 10;

DETAILED DESCRIPTION OF THE INVENTION

Figure 1:
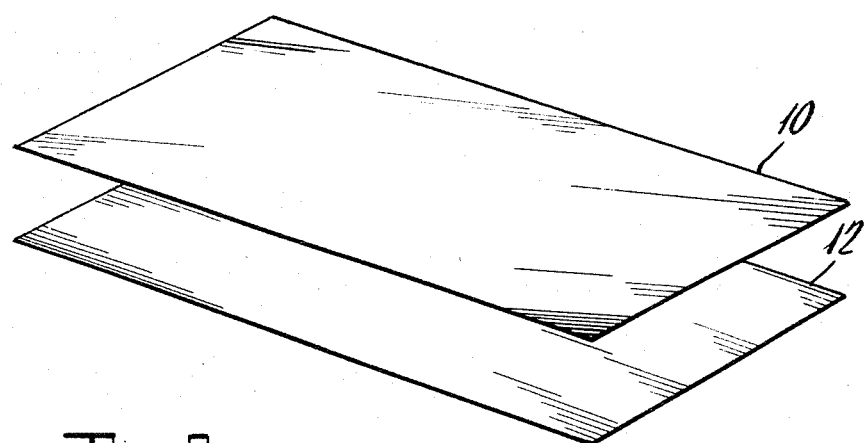
FIG. 1 is an exploded perspective view of an elastic composite according to the present invention.
Figure 2:
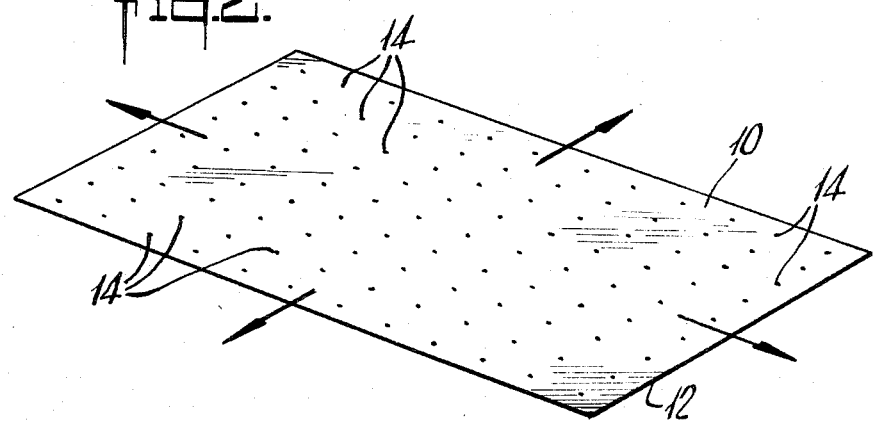
FIG. 2 is a perspective view of the elastic composite of FIG. 1 when stretched under tension.

FIG. 1 illustrates, in exploded perspective view, the elements of one embodiment of an elastic composite according to the present invention. The embodiment shown comprises a non-apertured elastic member 10 and an unstretched, non-gathered substrate 12 which before it is stretched is less easily extensible than the elastic member and has less elastic recovery than the elastic member. In a preferred embodiment, the substrate comprises a plastic film which may have a low melting point component such as ethylene vinyl acetate, to effect thermal bonding to the elastic. As shown in FIG. 2, the elastic member and substrate are intermittently bonded at 14 in a regular or irregular pattern. Bonding may be effected by any conventional means such as adhesive spot bonding, heat sealing, sonic bonding, etc. The substrate may alternatively comprise a woven, nonwoven, knitted or fusible fabric with the requisite extensibility and elastic recovery.

Figure 3:
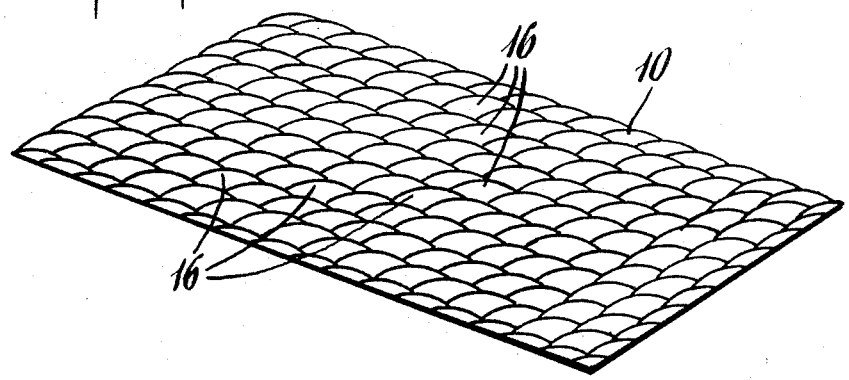
FIG. 3 is a perspective view of the elastic composite of FIG. 2 when the tension is released.

As shown in FIG. 2, the composite may be stretched in any direction, imparting extensibility and elasticity to the composite. The elastic must have sufficient strength to pucker or gather the substrate, as shown at 16 in FIG. 3, when the tension is released. The extensibility and recovery of the elastic composite may be incorporated into an elastic bandage or wrap that is easy to apply and fits closely. The puckering of the substrate provides bulk and softness in the bandage. The bandage may be extended and rendered elastic prior to or during bandaging, and different portions of the bandage may be given different degrees of extensibility and elasticity. The substrate used may have sufficient strength to substantially prevent extensibility of the composite during wearing, or may stretch easily allowing the bandage or composite to stretch in place, as worn, providing enhanced conformability and fit. The puckered composite, as shown in FIG. 3, may also be used to provide a "mock shirred" fabric, and if desired the final dimensions of the fabric may be the same as the starting dimensions of the substrate.

FIG. 4 illustrates a preferred embodiment of an elastic member to be used in forming an elastic composite of the present invention. The elastic shown generally at 20 is a reticulated elastic element having transverse strands 22 and longitudinal strands 24. As shown in exploded view in FIG. 5, the elastic composite of the present invention may be formed of an unstretched reticulated elastic 20, a substrate 28 having less extensibility than the elastic member and less elastic recovery than the elastic member, and a second substrate 30 which "sandwiches" the elastic member and which has substantially the same physical properties as substrate 28. FIG. 6 illustrates the assembled elastic composite of FIG. 5 peeled back to show the two substrates and the elastic member. In a preferred embodiment, the substrate may comprise a plastic film. In a still preferred embodiment, the elastic film may comprise a laminate having a low melting point component such as ethylene-vinyl acetate adjacent the elastic member to effect thermal bonding thereto. Alternatively, the elastic member may incorporate a low melting point component. In a most preferred embodiment, the substrate comprises a laminate having a layer of polypropylene for strength and an inner layer of ethylenevinyl acetate for bonding to the elastic member and an outer layer of polyethylene due to its good hand and release characteristics. The polyethylene may be embossed.

FIG. 7 illustrates the composite of FIG. 6 stretched in the longitudinal direction. The substrate extends and undergoes permanent elongation but remains intermittently bonded to the elastic member. If a reticulated elastic is used, such as shown in FIG. 6 at 20, bonding of the substrates through the openings in the reticulated elastic may be delaminated in the stretching of the composite leaving the elastic and the substrates bonded at the intermediate sites of the transverse and/or longitudinal strands. The substrate may possess some elastic recovery but in general must have less elastic recovery than the elastic member bonded thereto.

FIG. 8 illustrates the composite of FIG. 7 once the tension thereon has been released and the composite has returned to its original length. As is illustrated, the substrate or substrates have been permanently elongated and are puckered at 34 by the elastic when it contracts. FIG. 9 is an expanded view of the elastic composite shown in FIG. 8. As shown in FIG. 9, the puckering 34 occurs between the intermittent bonds which remain along the transverse strands 22 of the elastic member. It should be noted that if the method of attachment of the elastic member to the substrate is not capable of elongation, some or all of the bonding of the longitudinal strands to the substrates may be disrupted by the initial stretching.

FIG. 10 illustrates an exploded view of a disposable diaper and its method of manufacture according to the present invention. The diaper includes a facing layer 126, an impervious backing sheet 128, and an absorbent panel 130, and is provided with tape tabs 132. The generally rectangular diaper may be provided with unstretched or partially stretched elastic along the longitudinal edges thereof. In a preferred embodiment as shown, the elastic 134 may comprise reticulated elastic. During the manufacturing process, the elastic is at least intermittently bonded to the plastic film backing layer of the diaper. If the facing layer overlies the elastic, it must be extensible in the region which overlies the elastic. FIG. 11 illustrates the completed diaper assembled according to FIG. 10. The elastic composite is incorporated in the diaper along the longitudinal edges to form elastic composites 136 and 137 in the leg opening regions. Prior to diapering, or while being worn, the elastic composites may be selectively stretched in selected areas to impart a greater elasticity to the leg opening regions.

Figure 12:
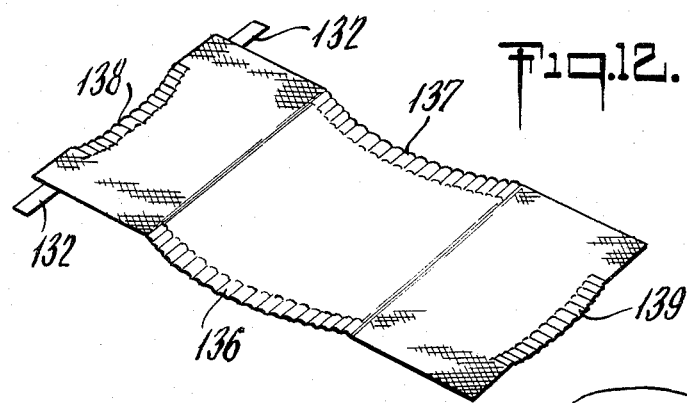
FIG. 12 is a preferred embodiment of a disposable diaper according to the present invention.

FIG. 12 illustrates a preferred embodiment of a diaper according to the present invention. The leg opening regions may comprise elastic composites 136 and 137 according to the present invention. The waist-fitting portions may also comprise elastic composites 138 and 139 according to the present invention. The elastic member may be incorporated with the composite in an unstretched or partially stretched condition. The elastic composite at the waist-fitting portions provides a diaper with good fit that may be adjusted by the diaperer. In addition, if the elastic is incorporated into the diaper in an unstretched condition, it may be easily set in transversely to machine direction.

Figure 13:
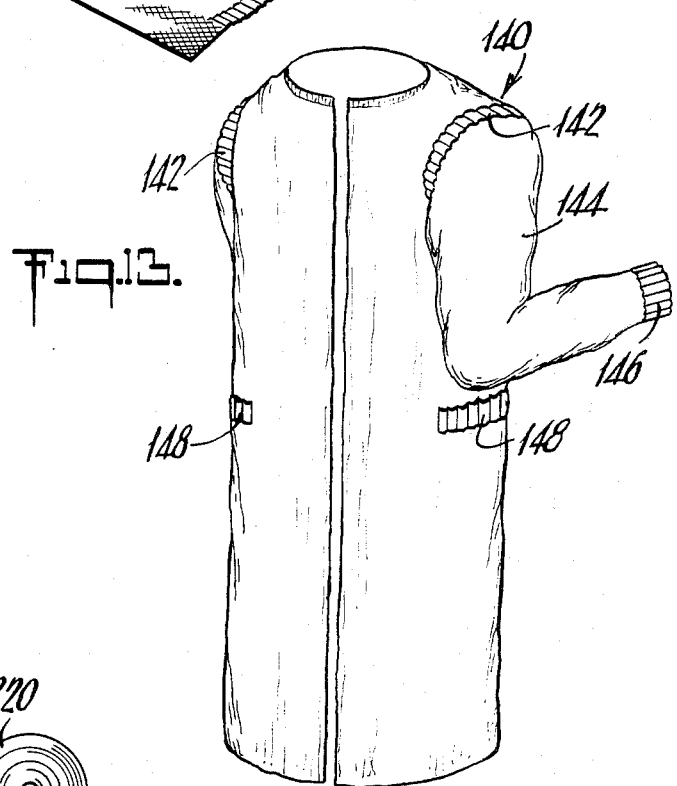
FIG. 13 is a perspective view of a disposable surgical gown incorporating the elastic composite of the present invention.

FIG. 13 illustrates a disposable gown such as a surgical or examination gown, utilizing the elastic composite of the present invention. The gown shown generally at 140 has an elastic composite incorporated into the armhole opening at 142. The elastic composite may be attached by any means such as heat sealing, gluing or stitching to both the main body 143 and sleeve 144 of the garment. If desired, the composite may strongly resist stretching, but after initial stretching provide elasticity as needed. Preferably, the composite stretches easily so that the garment grows to fit the wearer. The elastic composite may also be incorporated in the gown in other regions such as at 146 in the sleeve cuff and 148 around the waist.

Figure 14:
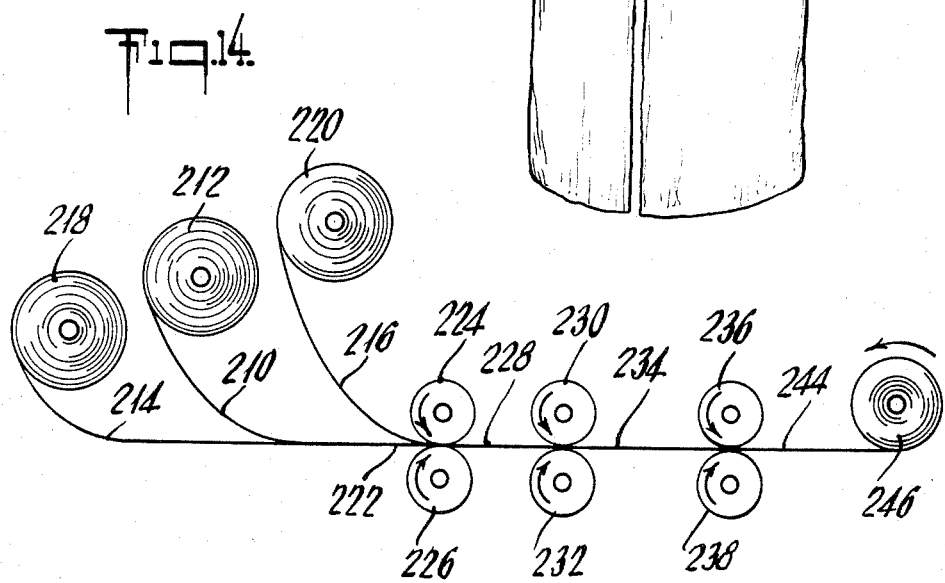
FIG. 14 is a schematic illustration of the process according to the present invention.

FIG. 14 is a mechanical schematic of one method according to the present invention. A supply roll 212 of reticulated elastic 210 is continuously inserted between two substrate layers, preferably plastic film layers 214, 216, fed from supply rolls 218, 220, respectively. Desirably, the plastic film includes a layer of ethylene-vinyl acetate copolymer, which faces toward the reticulated elastic 210, and a layer of a stretchable polymer such as polypropylene or high density polyethylene. The three layer web 222 comprising the reticulated elastic 210 contained between two plastic film substrates 214, 216 is fed into the nip of a pair of smooth, heated, counterrotating rolls 224, 226 to heat seal the reticulated elastic 210 to the two layers of film 214, 216, to form a heat sealed three layer composite 228.

In a preferred embodiment of the method of the present invention, the heat sealed composite 228 may then be fed into the nip of a second pair of counter-rotating rolls 230, 232, which may be cooled to insure that the thermal bonding is "set". The composite may be made as part of, or made and then incorporated into an article. The composite may be initially stretched by the user or applier, or may be stretched during the manufacturing process as follows. The web 234 emerging from the second pair of counter-rotating rolls 230, 232 may be fed into the nip of a third pair of counter-rotating rolls 236, 238, rotating at a faster peripheral speed than the second pair 230, 232 to effect drafting between the two pairs of rolls. This drafting stretches the films 214, 216 and ruptures the heat seal bonds between the films 214, 216. As illustrated, the composite with elastic is stretched in the longitudinal direction, which may also rupture the seal between the longitudinal strands and the film(s), leaving only the transverse strands bonded to the film layers 214, 216. As the stretched composite 244 emerges from the third pair of counter-rotating rolls 236, 238, the longitudinal or machine direction tension is relaxed, and the composite 244 is fed to a windup 246 that is rotating at a peripheral speed approximately equal to the peripheral speed of the second pair of counter-rotating rolls 230 and 232.

FIG. 14 illustrates only one method for making the elastic composite of the present invention. Alternative methods have been described with reference to the prior drawings and considerable variation is permitted, without departing from the spirit and scope of the invention. For instance, the invention is operative when only one layer of plastic film is employed to bond to the reticulated elastic. Alternatively, only one layer of film may be used, but before it is bonded to the reticulated elastic, it is folded over the elastic to form, in effect, a three layer web. If desired, the reticulated elastic may be preheated before it reaches the heat sealing station, which in FIG. 14 is shown as a pair of counter-rotating rolls 224, 226. The preheating can be done by infrared heating, hot air heating, or other known procedures.

What is claimed is:

1. A selectively stretchable elastic composite comprising an elastic member in a relaxed condition intermittently bonded to an unstretched or non-gathered substrate less extensible than said elastic member, said composite being rendered elastic by stretching, and wherein the original length of the composite is not foreshortened when said composite is rendered elastic.

2. The composite of claim 1 wherein said elastic member is a reticulated elastic.

3. The composite of claim 2 wherein said reticulated elastic comprises a mixture of thermoplastic rubber and an olefin polymer.

4. The composite of claim 1 wherein said substrate is a plastic film.

5. The composite of claim 4 wherein said film comprises a laminate comprising a low melting point component adjacent said elastic, said low melting point component having a lower melting point than said elastic member or said substrate, to effect heat sealing of the elastic member to the substrate.

6. The composite of claim 2 wherein said reticulated elastic member has a coating of a low melting point component, said low melting point component having a lower melting point than said reticulated elastic member or said substrate, to effect heat sealing of the elastic member to the substrate.

7. The composite of claim 5 or 6 wherein said low melting point component is EVA.

8. The composite of claim 5 wherein said laminate further comprises a polypropylene film and an embossed polyethylene film.

9. A gathered stretchable elastic composite comprising an elastic member in a relaxed condition intermittently bonded to a stretched, puckered substrate, wherein the original length of the composite is never foreshortened.

10. A process for making a selectively stretchable elastic composite which may be rendered elastic by stretching, but in which the original length of the composite is not foreshortened when said composite is rendered elastic comprising:
    (a) intermittently bonding an unstretched elastic member to a substrate less easily extensible than said elastic member to form an elastic composite.

11. A process for making a selectively stretchable elastic composite which may be rendered elastic by stretching, but in which the original length of the composite is not foreshortened when said composite is rendered elastic comprising:
    (a) intermittently bonding an unstretched elastic member to a substrate less easily extensible than said elastic member to form an elastic composite, and (b) stretching selected areas of said composite to a selected degree to effect permanent elongation of said substrate, and (c) allowing the composite to relax.

12. The process of claim 11 wherein said elastic member is a reticulated elastic.

13. A gathered stretchable elastic composite formed by the process of claim 10, 11, or 12.

14. A process for selectively enhancing the stretchability of an elastic composite comprising:
    (a) intermittently bonding stretched but further stretchable elastic member to a substrate less easily extensible than said elastic member, and (b) stretching selected areas of said composite to permanently elongate said substrate to a selected degree to provide entensibility and enhance stretchability in the selected areas.

15. A process for providing an extensible waist band in a disposable diaper having a plastic backing layer and an absorbent batt, and having longitudinal side edges and end edges wherein an elastic member in an unstretched condition is intermittently bonded to the backing layer along at least one end edge, said at least one end edge being rendered extensible and elastic by the stretching, wherein said at least one end edge is not foreshortened when rendered elastic.

16. A process for providing selectively stretchable leg opening regions in a disposable diaper, said diaper having two end edges and two side edges and elastic members disposed adjacent the side edges, said side edges of the diaper being composed of a material which prior to stretching is less easily extensible than said elastic, said process comprising intermittently bonding said elastic member to the side edges in a partial stretched condition, and stretching selected areas of the side edges to permanently elongate the selected areas to a selected degree to provide extensibility and enhanced elasticity of said selected areas.

* * * * *